(12) United States Patent
Ikeno et al.

(10) Patent No.: US 8,779,162 B2
(45) Date of Patent: Jul. 15, 2014

(54) CYANATE ESTER COMPOUNDS AND CURED PRODUCTS THEREOF

(75) Inventors: Taketo Ikeno, Niigata (JP); Makoto Tsubuku, Niigata (JP); Masayuki Katagiri, Niigata (JP); Tomoo Tsujimoto, Niigata (JP)

(73) Assignee: Mitsubishi Gas Chemical Company, Inc., Tokyo (JP)

(*) Notice: Subject to any disclaimer, the term of this patent is extended or adjusted under 35 U.S.C. 154(b) by 192 days.

(21) Appl. No.: 13/522,528

(22) PCT Filed: Jan. 18, 2011

(86) PCT No.: PCT/JP2011/050734
§ 371 (c)(1),
(2), (4) Date: Sep. 17, 2012

(87) PCT Pub. No.: WO2011/090022
PCT Pub. Date: Jul. 28, 2011

(65) Prior Publication Data
US 2013/0023640 A1    Jan. 24, 2013

(30) Foreign Application Priority Data
Jan. 20, 2010    (JP) .................................. 2010-010317

(51) Int. Cl.
*C07D 209/34*    (2006.01)

(52) U.S. Cl.
USPC ........................................................ 548/484

(58) Field of Classification Search
None
See application file for complete search history.

(56) References Cited

U.S. PATENT DOCUMENTS

| 4,016,173 | A  | 4/1977  | Darmory et al.   |
|-----------|----|---------|------------------|
| 7,277,230 | B2 | 10/2007 | Srinivasan et al.|
| 7,365,124 | B2 | 4/2008  | Srinivasan et al.|
| 7,547,755 | B2 | 6/2009  | Heuer            |
| 7,642,315 | B2 | 1/2010  | Davis et al.     |
| 2005/0222334 | A1 | 10/2005 | Srinivasan et al. |
| 2005/0228137 | A1 | 10/2005 | Srinivasan et al. |
| 2008/0033123 | A1 | 2/2008  | Srinivasan et al. |
| 2008/0081896 | A1 | 4/2008  | Heuer            |
| 2008/0312373 | A1 | 12/2008 | Davis et al.     |
| 2009/0110938 | A1 | 4/2009  | Nishimura et al. |
| 2012/0009836 | A1 | 1/2012  | Ueno et al.      |

FOREIGN PATENT DOCUMENTS

| CN | 1721404   | 1/2006 |
| CN | 101423668 | 5/2009 |
| CN | 101516967 | 8/2009 |
| EP | 1582549   | 10/2005 |
| EP | 2055728   | 5/2009 |
| JP | 62-297316 | 12/1987 |
| JP | 9-3162    | 1/1997 |
| JP | 2003-012819 | 1/2003 |
| JP | 2005-290378 | 10/2005 |
| JP | 2006-70115 | 3/2006 |
| JP | 2009-132886 | 6/2009 |
| WO | 2008/037364 | 4/2008 |
| WO | 2008/157328 | 12/2008 |

OTHER PUBLICATIONS

U.S. Appl. No. 13/520,867 to Michio Yaginuma et al., filed Jul. 6, 2012.
U.S. Appl. No. 13/581,926 to Takaaki Ogashiwa et al., filed Aug. 30, 2012.
Search report from International Application No. PCT/JP2011/050734, mail date is Mar. 22, 2011.
International Preliminary Report on Patentability PCT/JP2011/050734, mail date is Aug. 16, 2012.
Search report from E.P.O. in EP Application No. 11734628 8 mail date is Jul. 9, 2013.
Office Action issued Jul. 25, 2013 in Chinese patent application No. 201180006782.4 and English language translation.

*Primary Examiner* — Michael Barker
(74) *Attorney, Agent, or Firm* — Greenblum & Bernstein, P.L.C.

(57) ABSTRACT

There is provided a novel cyanate ester compound that can provide a cured product possessing excellent heat resistance. The cyanate ester compound is represented by general formula (1):

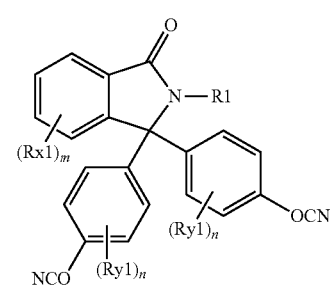

(1)

wherein R1 represents an aromatic substituent having 6 to 10 carbon atoms or an alkyl group having 1 to 20 carbon atoms; Rx1's each independently represent a hydrogen atom, an alkyl or alkoxy group having 1 to 20 carbon atoms, or a halogen; Ry1's each independently represent a hydrogen atom, an alkyl or alkoxy group having 1 to 20 carbon atoms, or a halogen; m is an integer of 0 to 4; and n is an integer of 0 to 4.

12 Claims, 8 Drawing Sheets

CYANATE ESTER COMPOUNDS AND CURED PRODUCTS THEREOF

TECHNICAL FIELD

The present invention relates to novel cyanate ester compounds. More specifically, the present invention relates to novel cyanate ester compounds possessing excellent heat resistance, heat-curable resin compositions comprising the cyanate ester compounds, and cured products thereof.

BACKGROUND OF THE INVENTION

With the expansion of applications of fiber-reinforced composite materials in recent years, various physical properties have become required of fiber-reinforced composite materials. One of the required properties is improved heat resistance. For fiber-reinforced composite materials, heat-curable resins such as phenol resins, melamine resins, bismaleimide resins, unsaturated polyester resins, cyanate ester resins, and epoxy resins are used as matrix resins depending upon specific use of fiber-reinforced composite materials, and the heat resistance of the fiber-reinforced composite materials relies upon the heat resistance of these matrix resins.

In order to improve the heat resistance of the matrix resins, an epoxy resin obtained by glycidylating 1,1,2,2-tetrakis(4-hydroxyphenyl)ethane (see, for example, Japanese Patent No. 3573530) and a composition comprising diaminophenyl sulfone, polyether sulfone, or polyether imide mixed into an epoxy resin composed mainly of an epoxy resin component having a triglycidylaminophenol skeleton (see, for example, Japanese Patent Application Laid-Open No. 297316/1987) have been proposed.

Cyanate ester resins are known as resins that, when cured, form cured resins which have a triazine ring and possess a high modulus of elasticity and a high level of heat resistance. Accordingly, cyanate ester resins are suitable for use as the heat-curable resins. Processes for producing fiber-reinforced composite materials using cyanate ester resins as a matrix have also been proposed (see, for example, Japanese Patent Application Laid-Open No. 12819/2003 and Japanese Patent Application Laid-Open No. 70115/2006).

Due to a recent tendency towards an increasing demand to these materials for a higher level of properties in fields of application thereof, a further improvement in physical properties of the matrix resins has been desired.

PRIOR ART DOCUMENTS

Patent Documents

Patent document 1: U.S. Pat. No. 3,573,530
Patent document 2: Japanese Patent Application Laid-Open No. 297316/1987
Patent document 3: Japanese Patent Application Laid-Open No. 12819/2003
Patent document 4: Japanese Patent Application Laid-Open No. 70115/2006

SUMMARY OF THE INVENTION

The present inventors have now found that novel cyanate ester compounds having a specific structure can impart excellent heat resistance to cured products thereof. The present invention has been made based on such finding.

Accordingly, an object of the present invention is to provide novel cyanate ester compounds that can provide cured products possessing excellent heat resistance. Another object of the present invention is to provide curable resin compositions comprising novel cyanate ester compounds, and cured products of the resin compositions.

According to a first aspect of the present invention, there are provided cyanate esters compounds represented by general formula (1):

wherein
R1 represents an aromatic substituent having 6 to 10 carbon atoms or an alkyl group having 1 to 20 carbon atoms;
Rx1's each independently represent a hydrogen atom, an alkyl or alkoxy group having 1 to 20 carbon atoms, or a halogen;
Ry1's each independently represent a hydrogen atom, an alkyl or alkoxy group having 1 to 20 carbon atoms, or a halogen;
m is an integer of 0 to 4; and n is an integer of 0 to 4.

According to a second aspect of the present invention, there are provided cyanate ester compounds represented by general formula (2):

wherein
R2 represents an aromatic substituent having 6 to 10 carbon atoms or an alkyl group having 1 to 20 carbon atoms;
Rx2's each independently represent a hydrogen atom, an alkyl or alkoxy group having 1 to 20 carbon atoms, or a halogen;
Ry2's each independently represent a hydrogen atom, an alkyl or alkoxy group having 1 to 20 carbon atoms, or a halogen;
m is an integer of 0 to 4; and n is an integer of 0 to 4.

According to the present invention, there are also provided curable resin compositions comprising the cyanate ester compounds, and cured products of the curable resin compositions.

The cyanate ester compounds according to the present invention can provide cured products having a high glass transition temperature through polymerization thereof or copolymerization thereof with other resins. Accordingly, the cured products are very useful as highly functional polymeric materials and are materials having excellent thermal, electrical, and mechanical properties.

The heat-curable resin compositions comprising the cyanate ester compounds according to the present invention can be used in extensive applications, for example, electrically insulating materials, resist resins, semiconductor sealing resins, adhesives for printed wiring boards, electrical laminated plates, and other applications such as matrix resins for prepregs, materials for build-up laminated plates, resins for fiber-reinforced plastics, sealing resins for liquid crystal display panels, resins for liquid-crystal color filters, coating materials, various coating materials, and adhesives. In particular, cured products of the heat-curable resin compositions have a high glass transition temperature and possesses high heat resistance and, thus are suitable for use in matrices of fiber-reinforced composite materials.

DETAILED DESCRIPTION OF THE INVENTION

<Cyanate Esters According to First Aspect>

The cyanate esters according to the first aspect of the present invention are represented by general formula (1):

(1)

In formula (1), R1 represents an aromatic substituent having 6 to 10 carbon atoms or an alkyl group having 1 to 20 carbon atoms. Among them, an aromatic substituent having 6 to 10 carbon atoms or an alkyl group having 1 to 10 carbon atoms is preferred. Specifically, phenyl, methyl, ethyl, n-propyl, and i-propyl groups may be mentioned.

In formula (1), Rx1's each independently represent a hydrogen atom, an alkyl or alkoxy group having 1 to 20 carbon atoms, or a halogen. Among them, a hydrogen atom or an alkyl group having 1 to 10 carbon atoms is preferred. A hydrogen atom or an alkyl group having 1 to 3 carbon atoms is particularly preferred. Specifically, a hydrogen atom and methyl, ethyl, n-propyl, and i-propyl groups may be mentioned. m is an integer of 0 to 4.

In formula (1), Ry1's each independently represent a hydrogen atom, an alkyl or alkoxy group having 1 to 20 carbon atoms, or a halogen.

Among them, a hydrogen atom or an alkyl group having 1 to 10 carbon atoms is preferred. A hydrogen atom or an alkyl group having 1 to 3 carbon atoms is particularly preferred. Specifically, a hydrogen atom and methyl, ethyl, n-propyl, and i-propyl groups may be mentioned. n is an integer of 0 to 4.

<Cyanate Esters According to Second Aspect>

The cyanate esters according to the second aspect of the present invention are represented by general formula (2):

(2)

In formula (2), R2 represents an aromatic substituent having 6 to 10 carbon atoms or an alkyl group having 1 to 20 carbon atoms. Among them, an aromatic substituent having 6 to 10 carbon atoms or an alkyl group having 1 to 10 carbon atoms is preferred. Specifically, phenyl, methyl, ethyl, n-propyl, and i-propyl groups may be mentioned.

In formula (2), Rx2's each independently represent a hydrogen atom, an alkyl or alkoxy group having 1 to 20 carbon atoms, or a halogen. Among them, a hydrogen atom or an alkyl group having 1 to 10 carbon atoms is preferred. A hydrogen atom or an alkyl group having 1 to 3 carbon atoms is particularly preferred. Specifically, a hydrogen atom and methyl, ethyl, n-propyl, and i-propyl groups may be mentioned. m is an integer of 0 to 4.

In formula (2), Ry2's each independently represent a hydrogen atom, an alkyl or alkoxy group having 1 to 20 carbon atoms, or a halogen. Among them, a hydrogen atom or an alkyl group having 1 to 10 carbon atoms is preferred. A hydrogen atom or an alkyl group having 1 to 3 carbon atoms is particularly preferred. Specifically, a hydrogen atom and methyl, ethyl, n-propyl, and i-propyl groups may be mentioned. n is an integer of 0 to 4.

<Process for Producing Cyanate Ester Compounds>

The compounds represented by general formula (1) may be produced by any process without particular limitation. For example, the compounds may be produced from phenol compounds represented by general formula (3) by a process known as cyanate synthesis:

(3)

wherein R1, Rx1, and Ry1 are as defined in formula (1).

Phenol compounds represented by general formula (3) may be obtained by a publicly known conventional method, i.e., by a dehydration reaction between phenolphthalein derivatives represented by general formula (4) and amine derivatives or aniline derivatives (see, for example, Japanese Patent Application Laid-Open No. 290378/2005). Alternatively, the phenol compounds may be synthesized by other publicly known processes.

(4)

wherein Rx1 and Ry1 are as defined above in formula (1).

Examples of amine derivatives usable in the synthesis of phenol compounds represented by general formula (3) include methylamine, ethylamine, propylamine, isopropylamine, butylamine, sec-butylamine, tert-butylamine, amylamine, hexylamine, heptylamine, octylamine, nonylamine, decylamine, and cyclohexylamine.

Examples of aniline derivatives usable in the synthesis of phenol compounds represented by general formula (3) include aniline, o-methylaniline, m-methylaniline, p-methylaniline, o-methoxyaniline, m-methoxyaniline, p-methoxyaniline, o-ethylaniline, m-ethylaniline, p-ethylaniline, 2,3-dimethylaniline, 2,4-dimethylaniline, 2,5-dimethylaniline, 3,4-dimethylaniline, 3,5-dimethylaniline, o-chloromethylaniline, m-chloromethylaniline, p-chloromethylaniline, o-trifluoromethylaniline, m-trifluoromethylaniline, p-trifluoromethylaniline, o-chloroaniline, m-chloroaniline, p-chloroaniline, o-fluoroaniline, m-fluoroaniline, p-fluoroaniline, o-bromoaniline, m-bromoaniline, p-bromoaniline, o-carbomethoxyaniline, m-carbomethoxyaniline, p-carbomethoxyaniline, o-acetoxyaniline, m-acetoxyaniline, p-acetoxyaniline, 1-naphthylamine, 2-naphthylamine, 2-aminophenol, 3-aminophenol, 4-aminophenol, 4-amino-2-fluorophenol, 4-amino-2-chlorophenol, 4-amino-3-chlorophenol, 1-amino-2-naphthol, 2-amino-1-naphthol, 3-amino-2-naphthol, 4-amino-1-naphthol, 5-amino-1-naphthol, 5-amino-2-naphthol, 6-amino-1-naphthol, 8-amino-2-naphthol, 2-amino-m-cresol, 2-amino-p-cresol, 3-amino-o-cresol, 3-amino-p-cresol, 4-amino-m-cresol, 4-amino-o-cresol, 5-amino-o-cresol, 6-amino-m-cresol, 4-amino-3,5-xylenol, and 3-hydroxy-4-methoxyaniline.

The compounds represented by general formula (2) may be produced by any process without particular limitation. For example, the compounds represented by general formula (2) may be produced from phenol compounds represented by general formula (5) by a process known as cyanate synthesis.

(5)

wherein R2, Rx2, and Ry2 are as defined in formula (2).

Phenol compounds represented by general formula (5) may be produced by any process without particular limitation and may be produced by conventional processes, for example, may be synthesized from indolin-2,3-diones represented by general formula (6) and phenol compounds (see, for example, Japanese Patent Application Laid-Open No. 179649/2002).

(6)

wherein R2 and Rx2 are as defined in formula (2).

In the process for producing phenol compounds represented by general formula (5), phenols usable in the reaction with indolin-2,3-diones represented by general formula (6) include, but are not limited to, phenol, o-cresol, m-cresol, p-cresol, o-fluorophenol, m-fluorophenol, p-fluorophenol, o-chlorophenol, m-chlorophenol, p-chlorophenol, o-bromophenol, m-bromophenol, p-bromophenol, p-tert-butylphenol, p-nonylphenol, 2,4-xylenol, 2,5-xylenol, 3,4-xylenol, 3,5-xylenol, and resorcinol.

Various processes have been proposed for the production of the compounds represented by general formula (6), and these publicly known processes may be utilized. Three typical examples of the processes for producing the compounds represented by general formula (6) will be described. However, it should be noted that the present invention is not limited to these processes.

According to a first process, the compounds represented by general formula (6) are produced by N-alkylating or N-arylating isatins represented by general formula (7).

(7)

wherein Rx2 is as defined in formula (2).

This synthesis process is described, for example, as reference examples in Japanese Patent Application Laid-Open No. 41072/1994, Japanese Patent Application Laid-Open No. 40644/1997 (N-alkylation), and Japanese Patent Application Laid-Open No. 193966/1990 (N-arylation). The present invention, however, is not limited thereto.

According to a second process, the compounds represented by general formula (6) are produced from anilines. Examples of the second process include, but are not limited to, a process in which, as shown in the following synthesis scheme, anilines are amidated with oxalyl chloride and the resultant amide is cyclized by heating or with a Lewis acid (U.S. Pat. No. 5,198,461 and International Publication WO2007/070362)

wherein R2 and Rx2 are as defined in formula (2); and a process in which, as shown in the following synthesis scheme, a halogenooxalate derivative is allowed to act on anilines to N-acylate the anilines and the resultant N,N-disubstituted oxamate derivative is cyclized with phosphorus pentachloride (Japanese Patent Application Laid-Open No. 41072/1994 and Ann. Chim. (Rome) 57, 492 (1967)).

wherein R2 and Rx2 are as defined in formula (2).

For the cyanation of the phenol compounds, a commonly used process for synthesizing cyanate compounds is described in IAN HAMERTON, "Chemistry and Technology of Cyanate Ester Resins", BLACKIE ACADEMIC & PROFESSIONAL.

Besides the above process, for example, U.S. Pat. No. 3,553,244 discloses a process in which the phenol compound is reacted with a cyanogen halide in a solvent in the presence of a base in such a state that the cyanogen halide is always present in excess over the base. Further, Japanese Patent Application Laid-Open No. 53497/1995 discloses a process in which the cyanate ester is synthesized using a tertiary amine as a base in excess over cyanogen chloride. Furthermore, Japanese translation of PCT publication No. 501138/2000 discloses a process in which a trialkylamine is reacted with a cyanogen halide by a continuous plug flow system. Japanese translation of PCT publication No. 504835/2001 discloses a process in which the phenol compound is reacted with a cyanogen halide in an nonaqueous solution in the presence of a tertiary amine and discloses that a tert-ammonium halide produced as a by-product in this reaction is treated with an cation/anion exchange pair. Furthermore, Japanese Patent No. 2991054 discloses a process that comprises reacting the phenol compound with a tertiary amine and a cyanogen halide by simultaneous addition of the tertiary amine and the cyanogen halide in the presence of a solvent separable from water, conducting water washing and separation of the product solution, and purifying the product by precipitation using secondary or tertiary alcohols or poor solvents for hydrocarbons. Furthermore, Japanese Patent Application Laid-Open No. 277102/2007 discloses a process for synthesizing a cyanate ester by reacting naphthols, a cyanogen halide, and a tertiary amine in a two-phase solvent composed of water and an organic solvent under acidic conditions.

The phenol compound represented by general formula (3) or (5) can be cyanated by reacting the phenol compound with cyanogen chloride in a solvent in the presence of a basic compound. Alternatively, the cyanate ester may also be synthesized by forming a salt of the phenol compound represented by general formula (3) or (5) with a basic compound in a water-containing solution and subsequently subjecting the salt to a two-phase interface reaction with a cyanogen chloride.

A general cyanate ester synthesis procedure consists of dissolving the phenol compound represented by general formula (3) or (5) in an organic solvent, adding a basic compound such as a tertiary amine to the solution, and allowing the mixture to react with excess cyanogen halide. In this method, the cyanogen halide is always present in excess, and, thus, it is regarded that the production of an imide carbonate by a reaction between phenolate anions and the cyanate ester can be inhibited. Since, however, the excess cyanogen halide is reacted with the tertiary amine to give a dialkyl cyanamide, the reaction temperature should be kept at 10° C. or below, preferably 0° C. or below, more preferably −10° C. or below.

In the cyanate ester synthesis procedure, alternatively, for example, the order of dropwise addition of the compounds may be selected at will. For example, a method may be adopted in which the phenol compound is dissolved in a solvent, and the solution, a basic compound such as a tertiary amine, and a cyanogen halide or a solution thereof are added dropwise alternately or simultaneously. Alternatively, a method may be adopted in which a mixed solution composed of the phenol compound and a basic compound such as a tertiary amine and a cyanogen halide or a solution thereof can be supplied simultaneously. In both the methods, a large amount of heat is generated by an exothermic reaction, and, thus, for example, from the viewpoint of inhibiting a side reaction, the reaction temperature should be kept at 10° C. or below, preferably 0° C. or below, more preferably −10° C. or below.

The reaction may be of a batch or semi-batch type or alternatively may be of a continuous flow type without particular limitation.

A basic compound such as a tertiary amine and a cyanogen halide are added in an amount of 0.1 to 8 times by mole, preferably 1 to 5 times by mole, the amount of a phenolic hydroxyl group in the phenol compound, and a reaction between them is allowed to proceed. In particular, when the phenol compound has a sterically hindered substituent at the o-position of the hydroxyl group, the necessary amount of the basic compound such as the tertiary amine and the cyanogen halide is larger than the necessary amount thereof in the case where the substituent is absent. Cyanogen chloride, cyanogen bromide and the like may be used as the cyanogen halide. The basic compound used may be any of organic bases and inorganic bases. When an organic solvent is used, the use of organic bases that are highly soluble in the solvent is preferred. Among organic bases, tertiary amines that cause little or no side reaction are preferred. The tertiary amine may be any of alkylamines, arylamines, and cycloalkylamines. Specific examples thereof include trimethylamine, triethylamine, methyl diethylamine, tripropylamine, tributylamine, methyl dibutylamine, dinonylmethylamine, dimethyl stearylamine, dimethylcyclohexylamine, diisopropylethylamine, diethylaniline, pyridine, and quinoline.

Examples of solvents usable in the reaction include, but are not limited to, ketone solvents such as acetone, methyl ethyl ketone, and methyl isobutyl ketone, aromatic solvents such as benzene, toluene, and xylene, ether solvents such as diethyl ether, dimethyl cellosolve, diglyme, tetrahydrofuran, methyltetrahydrofuran, dioxane, and tetraethylene glycol dimethyl ether, halogenated hydrocarbon solvents such as methylene chloride, chloroform, carbon tetrachloride, and chlorobenzene, alcohol solvents such as methanol, ethanol, 2-propanol, methyl cellosolve, propylene glycol methyl ether, aprotic polar solvents such as N,N-dimethylformamide, N-methylpyrrolidone, 1,3-dimethyl-2-imidazolidone, and dimethyl sulfoxide, nitrile solvents such as acetonitrile and benzonitrile, nitro solvents such as nitromethane and nitrobenzene, ester solvents such as ethyl acetate and ethyl benzoate, and hydrocarbon solvents such as cyclohexane. One of or a combination of two or more of the solvents may be used depending upon the reactants.

The reaction system may be cooled by directly immersing a flask used in the reaction in an ice bath, a salt-ice bath, a solid carbon dioxide-acetone bath, a solid carbon dioxide-methanol bath, or a properly temperature-regulated acetone or methanol bath. Alternatively, the reaction system may be cooled by providing a jacketed apparatus and circulating a properly temperature-regulated methanol, ethanol, methanol-water, ethanol-water water, ethylene glycol-water, NAIBURAIN or other antifreezing solutions through the jacket. In addition to the above methods, a method may also be adopted in which satisfactorily precooled solutions are mixed by taking into consideration the heat of reaction.

In treatment after the reaction, by-produced hydrochloride of basic compounds such as tertiary amines is removed by filtration or washing with water. On the other hand, when a solvent miscible with water is used, an objective product can be obtained by adding the resultant reaction solution dropwise to water and then extracting the mixture with an organic solvent immiscible with water, or by collecting the precipitated crystals by filtration. In the step of washing, a method may also be adopted in which an acidic aqueous solution such as diluted hydrochloric acid is used to remove excess amines. In order to remove water from a thoroughly washed reaction solution, drying may be carried out by a conventional method such as the addition of sodium sulfate or magnesium sulfate.

After the above procedure, the reaction solution is subjected to concentration, precipitation, or crystallization. Due to unstable nature of the cyanate ester compound, the reaction solution is concentrated under the reduced pressure while maintaining the temperature at 150° C. or below. A solvent having low solubility may be used in the precipitation or crystallization. For example, a method may be adopted in which an ether solvent, a hydrocarbon solvent such as hexane, or an alcohol solvent is added dropwise to the reaction solution, or vice versa.

In order to wash the resultant crude product, a method may be adopted in which the concentrate or crystal obtained from the reaction solution is washed with an ether solvent, a hydrocarbon solvent such as hexane, or an alcohol solvent. Alternatively, a method may be adopted in which the reaction solution is concentrated to obtain crystals and the resultant crystals are again dissolved, followed by recrystallization. The reaction solution may simply be concentrated or cooled for crystallization. A highly pure cyanate ester compound can be obtained by removing volatile matter from the resultant product by drying under the reduced pressure or the like.

<Curable Resin Composition>

Next, the curable resin composition according to the present invention will be described. The curable resin composition according to the present invention comprises the above cyanate ester compound. The curable resin composition may further contain, for example, a cyanate ester compound other than the cyanate ester compound according to the present invention, an epoxy resin, an oxetane resin, and/or a compound containing a polymerizable unsaturated group.

Examples of cyanate ester compounds other than the cyanate ester compound according to the present invention include, but are not limited to, bisphenol A dicyanate, bisphenol F dicyanate, bisphenol M dicyanate, bisphenol P dicyanate, bisphenol E dicyanate, phenol novolak cyanate, cresol novolak cyanate, dicyclopentadiene novolak cyanate, tetramethylbisphenol F dicyanate, and biphenol dicyanate. One of or a combination of two or more of these cyanate ester compounds may be used.

Examples of such epoxy resins include, but are not limited to, bisphenol A epoxy resin, bisphenol F epoxy resin, biphenyl epoxy resin, phenol novolak epoxy resin, cresol novolak epoxy resin, xylene novolak epoxy resin, triglycidyl isocyanurate, alicyclic epoxy resin, dicyclopentadiene novolak epoxy resin, biphenyl novolak epoxy resin, phenol aralkyl novolak epoxy resin, and naphthol aralkyl novolak epoxy resin. One of or a combination of two or more of these epoxy resins may be used.

Examples of such oxetane resins include, but are not limited to, oxetane, alkyloxetanes such as 2-methyloxetane, 2,2-dimethyloxetane, 3-methyloxetane, and 3,3-dimethyloxetane, 3-methyl-3-methoxymethyloxetane, 3,3'-di(trifluoromethyl)perfluoroxetane, 2-chloromethyloxetane, 3,3-bis(chloromethyl)oxetane, OXT-101 (trademark; manufactured by TOAGOSEI CO., LTD.), and OXT-121 (trademark; manufactured by TOAGOSEI CO., LTD.). One of or a combination of two or more of these oxetane resins may be used.

Publicly known curing catalysts may be used to cure the curable resin composition comprising the cyanate ester compound. Examples of such curing catalysts include metal salts such as zinc octylate, zinc naphthenate, cobalt naphthenate, copper naphthenate, acetyl acetone iron and active hydroxyl group-containing compounds such as phenol, alcohol, and amines;

When the curable resin composition contains an epoxy resin and/or oxetane resin, epoxy resin curing agents and/or oxetane resin curing agents may be used. Examples of such epoxy resin curing agents include, but are not limited to, imidazole derivatives such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethylimidazole, and 2-phenyl-4-methyl-5-hydroxymethylimidazole, amine compounds such as dicyandiamide, benzyldimethylamine, and 4-methyl-N,N-dimethylbenzylamine, and phosphine-type such as phosphonium-type phosphorus compounds. Publicly known cation polymerization initiators may be used as the oxetane resin curing agent. Commercially available products may also be used, and suitable examples thereof include San-Aid SI60L, San-Aid SI-80L, and San-Aid SI100L (manufactured by Sanshin Chemical Industry), CI-2064 (manufactured by Nippon Soda Co., Ltd.), Irgacure 261 (manufactured by Ciba Specialty Chemicals), and Adekaoptomer SP-170 and Adekaoptomer SP-150 (manufactured by Asahi Denka). The cation polymerization initiator may also be used as the epoxy resin curing agent. One of or a combination of two or more of these curing agents may be used.

Polymerizable unsaturated group-containing compounds that may be contained in the curable resin composition include, for example, vinyl compounds such as ethylene, propylene, styrene, divinylbenzene, and divinylphenyl, (meth)acrylates of mono- or polyhydric alcohols such as methyl(meth)acrylate, 2-hydroxyethyl(meth)acrylate, 2-hydroxypropyl(meth)acrylate, polypropylene glycol di(meth)acrylate, trimethylolpropane di(meth)acrylate, trimethylolpropane tri(meth)acrylate, pentaerythritol tetra(meth)acrylate, and dipentaerythritol hexa(meth)acrylate, epoxy (meth)acrylates such as bisphenol A-type epoxy(meth)acrylate, and bisphenol F-type epoxy(meth)acrylate, benzocyclobutene resins, and (bis)maleimide resins. One of or a combination of two or more of these compounds may be used.

When the curable resin composition contains a polymerizable unsaturated group-containing compound, if necessary, publicly known polymerization initiators may be used. Examples of such polymerization initiators include, but are not limited to, peroxides such as benzoyl peroxide, p-chlorobenzoyl peroxide, di-t-butyl peroxide, di-isopropyl peroxycarbonate, di-2-ethylhexyl peroxycarbonate, or azo compounds such as azobisisobutyronitrile.

<Cured Product>

The cured product according to the present invention is obtained by curing the curable resin composition by exposing the composition to heat, light or the like. In heat curing, when the curing temperature is excessively low, curing does not proceed while, when the curing temperature is excessively high, the cured product is deteriorated. Thus, the curing temperature is preferably in the range of 150° C. to 300° C.

The cured product obtained by curing the resin composition comprising the cyanate ester compound according to the present invention is preferably used in electrical insulating materials, sealing materials, adhesives, lamination materials, resists, build-up laminated plate materials, as well as in fixing materials in the fields of civil engineering-construction, electricity-electronics, automobiles, railways, shippings, aircrafts, sporting goods, arts and crafts and the like, structural members, reinforcing materials, and embossing materials. In particular, the cured product of the resin composition can be used in a wide range of applications such as aircraft structural members, satellite structural members, and railway/vehicle structural members, of which weatherability, flame resistance, and high mechanical strength are required, and fiber reinforced composite materials for sporting goods, that is, golf club shafts and fishing rods.

EXAMPLES

The present invention is further illustrated by the following Examples that are not intended as a limitation of the invention.

Synthesis Example 1

Synthesis of 2-phenyl-3,3-bis(4-hydroxyphenyl)phthalimidine

Concentrated hydrochloric acid (36%, 20.5 mL, 232 mmol) was added dropwise to an aniline (65 mL, 717 mmol) solution of phenolphthalein (31.86 g, 100 mmol). Water was removed by distillation while heating the mixture at an internal temperature of 155 to 165° C. in an oil bath. The reaction solution was analyzed by liquid chromatography while heating the reaction solution with stirring until phenolphthalein, the starting material, disappeared (about 16 hr). Thereafter, the reaction solution was poured into a mixed solution composed of concentrated hydrochloric acid (36%, 51.4 mL) and water (600 mL). The mixture was stirred for 30 min, was filtered, and washed with water to obtain crystals. The crystals were dissolved in an aqueous solution (800 mL) of sodium hydroxide (16.04 g, 401 mmol). Activated carbon (5.22 g) was added thereto, and the mixture was stirred for 1 hr. The activated carbon was removed by filtration. Fresh activated carbon (5.60 g) was then added to the filtrate, and the mixture was stirred for 1 hr. The activated carbon was removed by filtration, and concentrated hydrochloric acid (36%) was then slowly added dropwise to the filtrate until the filtrate became acidic. The mixture was stirred overnight and was then filtered, and the crystals were washed with water until the pH of the washings was no longer acidic (four times). The crystals were dried under vacuum with an oil-sealed rotary vacuum pump. The crystals were added to 150 mL of methanol (99.9%; manufactured by Mitsubishi Gas Chemical Co., Inc.). The mixture was stirred with heating under reflux for 1 hr and was then allowed to cool to room temperature. The precipitated crystals were collected by filtration, were washed with methanol, and were dried to obtain a product (36.32 g, 92.3 mmol, yield 92%)

Figure 1:
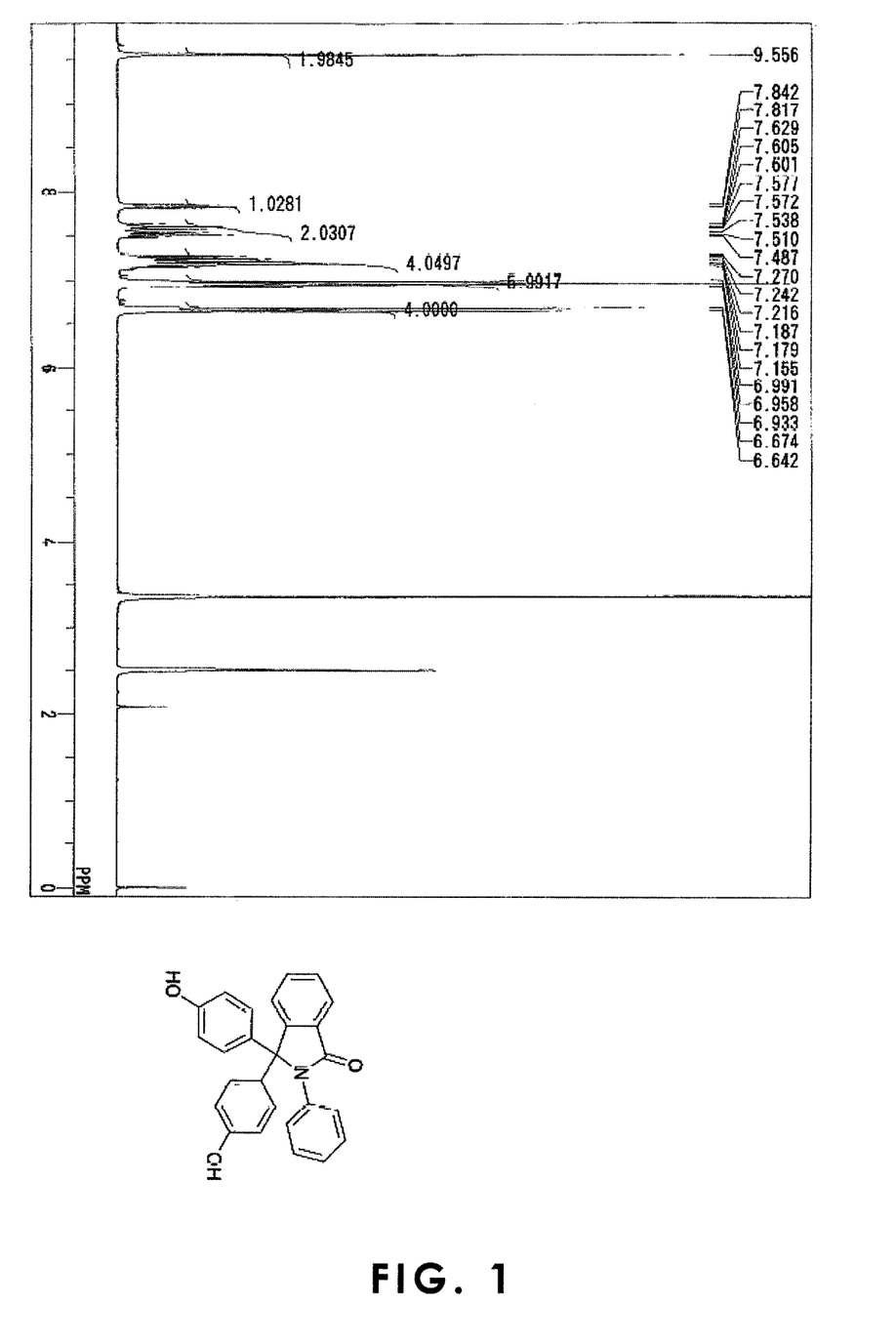
FIG. 1 is an H1-NMR chart of 2-phenyl-3,3-bis(4-hydroxyphenyl)phthalimidine obtained in Synthesis Example 1.

The structure of the compound thus obtained was identified by an NMR spectrum with a nuclear magnetic resonance apparatus (JNM-EX270FT-NMR; manufactured by Japan Electric Optical Laboratory). The NMR spectrum was as shown in FIG. 1.

$^1$H-NMR: (270 MHz, DMSO-d6, internal standard TMS) δ (ppm) 6.66 (d, 4H, J=8.6 Hz), 6.92-7.01 (m, 6H), 7.14-7.28 (m, 4H), 7.47-7.65 (m, 2H), 7.83 (d, 1H, J=6.9 Hz), 9.56 (s, 2H)

Synthesis Example 2

Synthesis of 2-(4-Methylphenyl)-3,3-bis(4-hydroxyphenyl)phthalimidine (abbreviated to BisP-PI-Np-Tol)

p-Toluidine (31.8 g, 717 mmol) was heated to 80° C. for melting, and concentrated hydrochloric acid (36%, 20.5 mL, 232 mmol) was added dropwise thereto. Thereafter, phenolphthalein (31.8 g, 100 mmol) was added, and water was removed by distillation from the mixture while heating the mixture at an internal temperature of 155 to 165° C. in an oil bath. The reaction solution was analyzed by liquid chromatography while heating the reaction solution with stirring until phenolphthalein, the starting material, substantially disappeared (about 18 hr; HPLC assay: phenolphthalein 4 area %, p-toluidine 20 area %, product 76 area %). The reaction solution was poured into a mixed solution composed of concentrated hydrochloric acid (36%, 51.4 mL) and water (600 mL). The mixture was stirred for 3 days, was filtered, and was washed with water to obtain crystals. The crystals were dissolved in an aqueous solution (1 L) of sodium hydroxide (10.06 g, 252 mmol). Activated carbon (5.01 g) was added thereto, and the mixture was stirred for 1 hr. The activated carbon was removed by filtration. Fresh activated carbon (5.43 g) was then added to the filtrate, and the mixture was stirred for 1 hr. The activated carbon was removed by filtration, and concentrated hydrochloric acid (36%) was then slowly added dropwise to the filtrate until the filtrate became acidic. The mixture was stirred overnight and was then filtered, and the crystals were washed with water until the pH of the washings was no longer acidic (four times). The crystals were dried under vacuum with an oil-sealed rotary vacuum pump to obtain a product. L-7000 series, D-200 Chromato-integrator, manufactured by Hitachi, Ltd. was used in the liquid chromatography (TSKgel ODS-120T column manufactured by Tosoh Corporation). An acetonitrile-water mixed solvent was used as a developing solvent (flow rate 1 ml/min).

Figure 2:
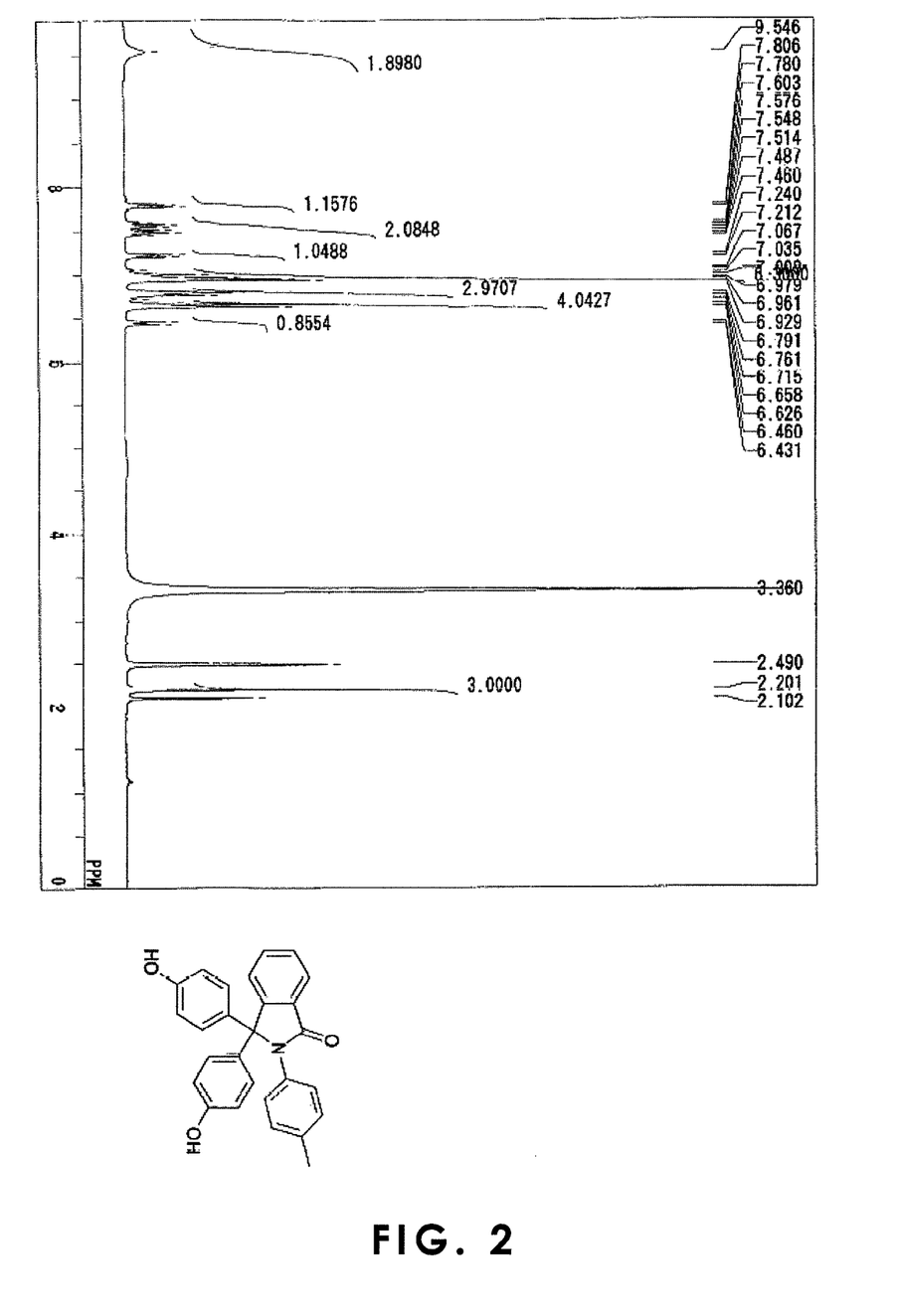
FIG. 2 is an H1-NMR chart of 2-(4-methylphenyl)-3,3-bis(4-hydroxyphenyl)phthalimidine obtained in Synthesis Example 2.

The structure of the compound thus obtained was identified by an
NMR spectrum in the same manner as described above. The NMR spectrum was as shown in FIG. 2.

$^1$H-NMR: (270 MHz, DMSO-d6, internal standard TMS)
δ (ppm) 2.20 (s, 3H), 6.45 (d, 1H, J=7.9 Hz), 6.64 (d, 4H, J=8.6 Hz), 6.73-6.83 (m, 2H), 6.90-7.05 (m, 5H), 7.23 (d, 1H, J=7.6 Hz), 7.43-7.63 (m, 2H), 7.79 (d, 1H, J=7.3 Hz), 9.55 (s, 2H)

Synthesis Example 3

Synthesis of 2-phenyl-3,3-bis(4-hydroxy-3-methylphenyl)phthalimidine (abbreviated to BisOCR-PI-NPh)

Concentrated hydrochloric acid (36%, 15.0 mL, 170 mmol) was added dropwise to an aniline (47.5 mL, 524 mmol) solution of o-cresol phthalein (25.31 g, 73.1 mmol). Water was removed by distillation while heating the mixture at an internal temperature of 155 to 165° C. in an oil bath. The reaction solution was analyzed by liquid chromatography while heating the reaction solution with stirring until phenolphthalein, the starting material, disappeared (about 20 hr). The reaction solution was poured into a mixed solution composed of concentrated hydrochloric acid (36%, 20 mL) and water (600 mL). The mixture was stirred for 4 days, was filtered, and washed with water to obtain crystals. The crystals were dissolved in an aqueous solution (200 mL) of sodium hydroxide (8.00 g, 200 mmol). Activated carbon (5 g) was added thereto, and the mixture was stirred for 30 min. The activated carbon was removed by filtration. Fresh activated carbon (5 g) was then added to the filtrate, and the mixture was stirred for 30 min. The activated carbon was removed by filtration, and concentrated hydrochloric acid (36%) was then slowly added dropwise to the filtrate until the filtrate became acidic. The mixture was stirred for 3 hr and was then filtered, and the crystals were washed with water until the pH of the washings was no longer acidic (four times). The crystals were then air-dried to obtain a product (29.12 g, 69.1 mmol, yield 95%, HPLC (high-performance liquid chromatography) assay: not less than 98 area %). The HPLC assay was carried out in the same manner as described above.

Figure 3:
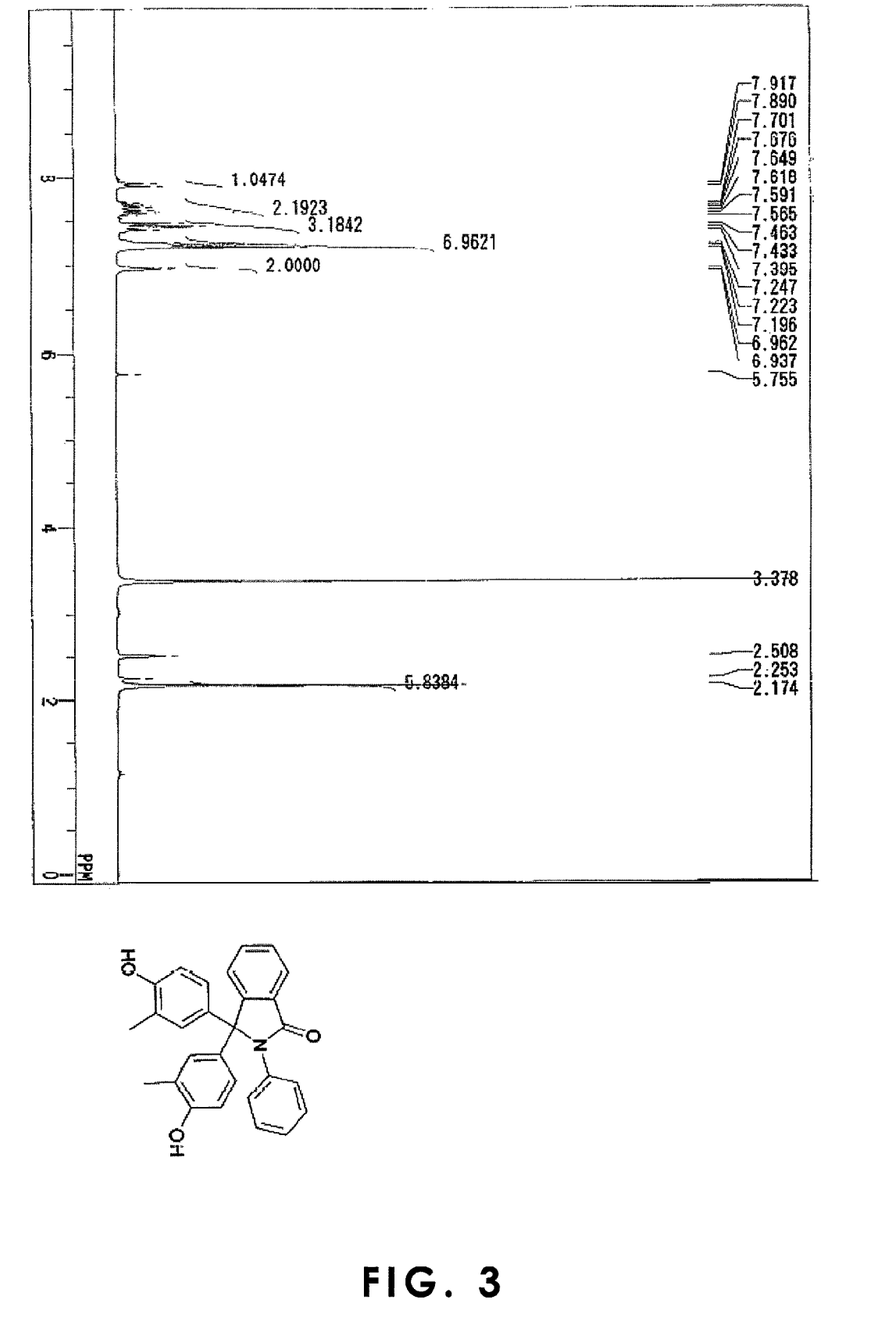
FIG. 3 is an H1-NMR chart of 2-phenyl-3,3-bis(4-hydroxy-3-methylphenyl)phthalimidine obtained in Synthesis Example 3.

The structure of the compound thus obtained was identified by an NMR spectrum in the same manner as described above. The NMR spectrum was as shown in FIG. 3.

$^1$H-NMR: (270 MHz, DMSO-d6, internal standard TMS)
δ (ppm) 2.17 (s, 6H), 6.95 (d, 2H, J=6.6 Hz), 7.15-7.29 (m, 7H), 7.37-7.48 (m, 3H), 7.55-7.72 (m, 2H), 7.90 (d, 1H, J=7.3 Hz)

Synthesis Example 4

Synthesis of N-methylisatin

A dimethylformamide (hereinafter referred to as DMF) (500 ml) solution of isatin (14.70 g, 100 mmol, purity 98%; manufactured by SIGMA-ALDRICH) was cooled to 0° C. in an ice bath, and sodium hydride (4.73 g, 118 mmol, 60% in oil; manufactured by Tokyo Chemical Industry Co., Ltd.) was added by portions with a spatula over a period of 10 min. After stirring for 15 min, methyl iodide (7.5 mL, 120 mmol) was added by portions with a Komagome pipette over a period of 10 min. The mixture was stirred at 0° C. for 1 hr and was then poured into 1 L of an aqueous hydrochloric acid solution. The mixture was extracted with ethyl acetate, and an ethyl acetate phase was washed twice with water. The ethyl acetate phase was concentrated to obtain 13.6 g of a crude product of N-methylisatin (HPLC assay: 79 area %). The HPLC assay was carried out in the same manner as described above.

Synthesis Example 5

Synthesis of 1-methyl-3,3-bis(4-hydroxyphenyl)indolin-2-one (abbreviated to BisP-IST-NMe)

The crude product of N-methylisatin (13.6 g, 84.5 mmol) obtained in Synthesis Example 4 was dissolved in phenol (32.78 g, 348 mmol). The solution was added by portions to a mixed solution composed of phenol (15.14 g, 161 mmol) and concentrated hydrochloric acid (36%, 15.0 mL, 170 mmol) at 35° C. over a period of 2.5 hr. The mixture was then stirred at 35° C. for 3 hr and was stirred at room temperature overnight. An aqueous 75% phosphoric acid solution (0.081 ml) and an aqueous 16% potassium hydroxide solution (8.8 ml) were added thereto, and the mixture was heated at 100° C. for 1 hr. Toluene (124 ml) was added thereto, and the mixture was allowed to cool. The resultant crystals were collected by filtration and was thoroughly washed with toluene. The product thus obtained was washed with hot water under stirring, was then collected by filtration, was washed with hot water, and was air-dried to obtain a product (18.65 g, 56.3 mmol, 67%, HPLC assay: 98 area %). The HPLC assay was carried out in the same manner as described above. The synthesis scheme is as follows.

-continued

Figure 4:
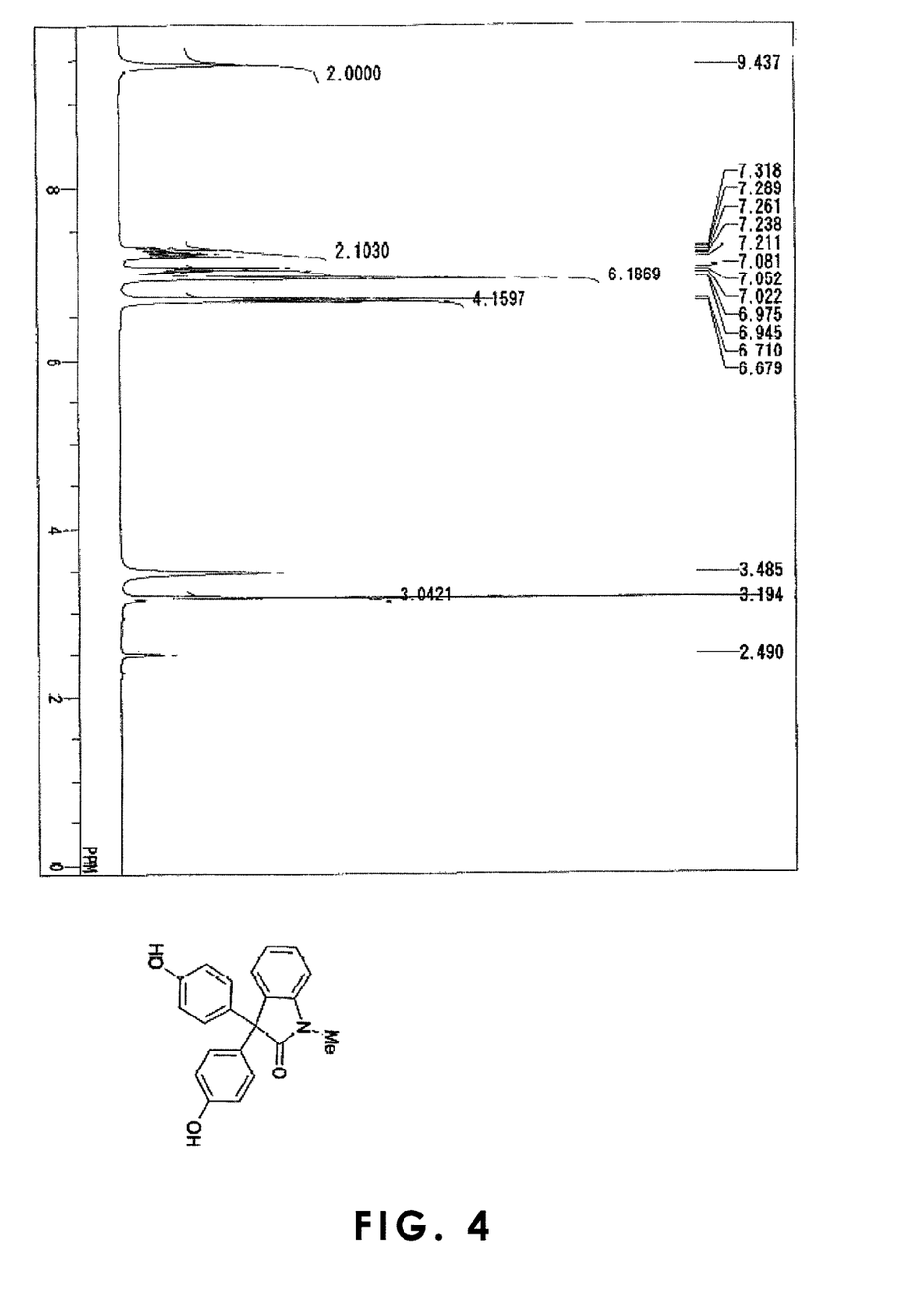
FIG. 4 is an H1-NMR chart of 1-methyl-3,3-bis(4-hydroxyphenyl)indolin-2-one obtained in Synthesis Example 5.

The structure of the compound thus obtained was identified by an NMR spectrum in the same manner as described above. The NMR spectrum was as shown in FIG. 4.

$^1$H-NMR: (270 MHz, DMSO-d6, internal standard TMS) δ (ppm) 3.19 (s, 3H), 6.69 (d, 4H, J=8.6 Hz), 6.90-7.10 (m, 6H), 7.19-7.33 (m, 2H), 9.44 (s, 2H)

Cyanate Ester Production Example 1

Synthesis of 2-phenyl-3,3-bis(4-cyanatophenyl)phthalimidine (abbreviated to BisP-PI-NPh-DC)

2-Phenyl-3,3-bis(4-hydroxyphenyl)phthalimidine (30 mmol) obtained in Synthesis Example 1 was suspended in dichloromethane (90 mL). Triethylamine (90 mmol) was added to the suspension with cooling in an ice bath, and, after the completion of an exothermic reaction, the temperature of the reaction solution was raised to room temperature. Separately, 36% hydrochloric acid (90 mmol), water (50 mL), a 40% dichloromethane solution of cyanogen chloride (90 mmol; manufactured by Mitsubishi Gas Chemical Co., Inc.), and dichloromethane (8 mL) were placed in a jacketed flask. Methanol of −10° C. was circulated through the jacket to cool the contents in the flask. The solution prepared above was added dropwise thereto under stirring while regulating the temperature of the contents of the flask at 0° C. or below. The reaction solution was stirred for 1 hr, and a dichloromethane (9 mL) solution of triethylamine (30 mmol) was further added dropwise thereto. The completion of the reaction was confirmed by liquid chromatography. The temperature of the reaction solution was raised to room temperature before the organic phase was separated. Cyanogen chloride was removed by distillation under the reduced pressure, and the residue was washed five times with water (100 mL). The organic phase was concentrated to obtain a product. The confirmation by the liquid chromatography was carried out in the same manner as described above.

Figure 5:
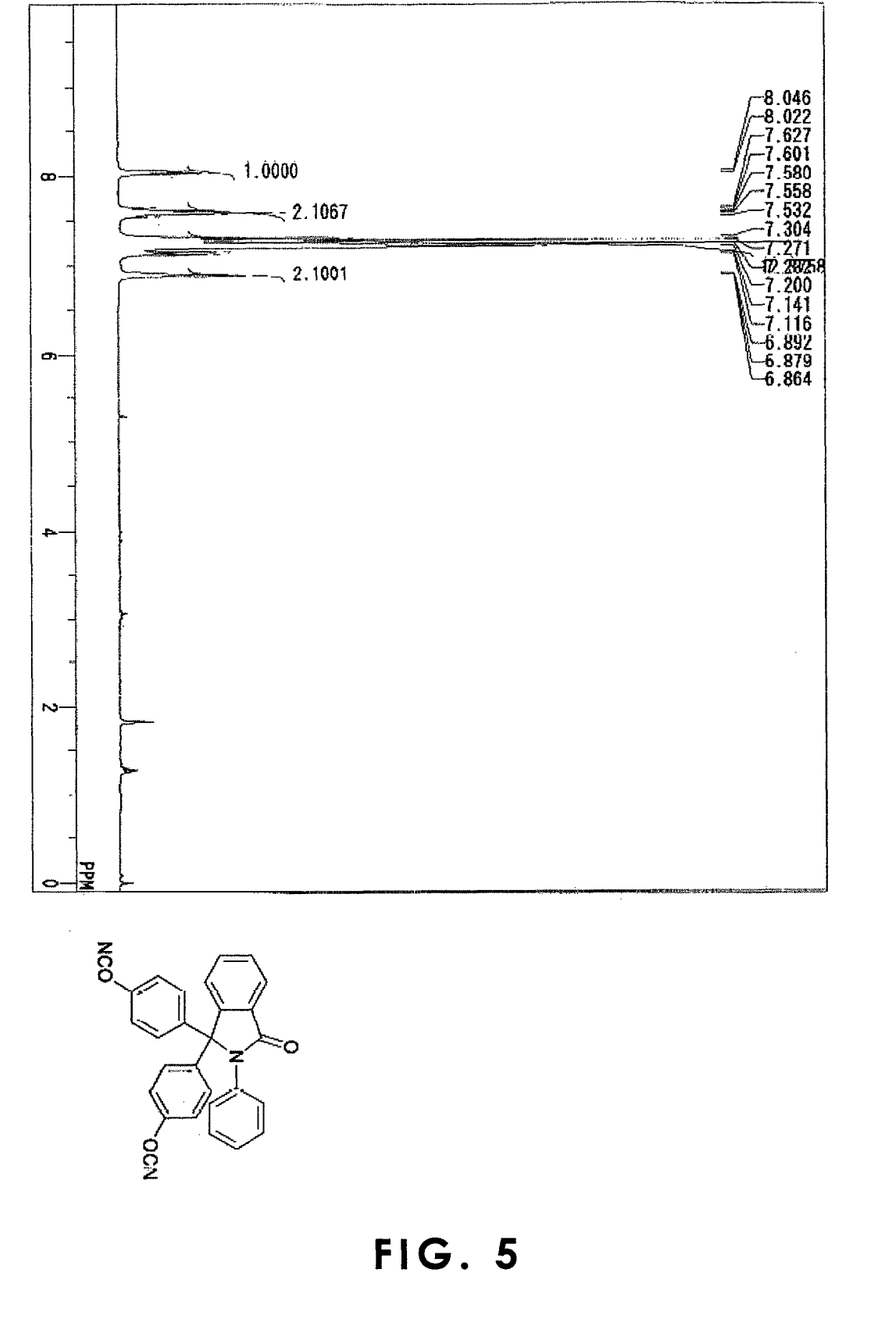
FIG. 5 is an H1-NMR chart of 2-phenyl-3,3-bis(4-cyanatophenyl)phthalimidine obtained in Production Example 1.

The structure of the compound thus obtained was identified by an NMR spectrum in the same manner as described above. The NMR spectrum was as shown in FIG. 5.

$^1$H-NMR: (270 MHz, chloroform-d, internal standard TMS)
δ (ppm) 6.82-6.94 (m, 2H), 7.07-7.36 (m, 12H), 7.48-7.66 (m, 2H), 8.03 (d, 1H, J=6.6 Hz)

Cyanate Ester Production Example 2

Synthesis of 2-(4-methylphenyl)-3,3-bis(4-cyanatophenyl)phthalimidine (abbreviated to BisP-PI-NpTol-DC)

2-(4-Methylphenyl)-3,3-bis(4-hydroxyphenyl)phthalimidine (30 mmol) obtained in Synthesis Example 2 was suspended in dichloromethane (90 mL). Triethylamine (90 mmol) was added to the suspension with cooling in an ice bath, and, after the completion of an exothermic reaction, the temperature of the reaction solution was raised to room temperature. Separately, 36% hydrochloric acid (90 mmol), water (50 mL), a 40% solution of cyanogen chloride (90 mmol) in dichloromethane, and dichloromethane (8 mL) were placed in a jacketed flask. Methanol of −10° C. was circulated through the jacket to cool the contents in the flask. The solution prepared above was added dropwise thereto under stirring while regulating the temperature of the contents of the flask at 0° C. or below. The reaction solution was stirred for 1 hr, and a dichloromethane (9 mL) solution of triethylamine (30 mmol) was further added dropwise thereto. The completion of the reaction was confirmed by liquid chromatography. The temperature of the reaction solution was raised to room temperature before the organic phase was separated. Cyanogen chloride was removed by distillation under the reduced pressure, and the residue was washed five times with water (100 mL). The organic phase was concentrated to obtain a product. The confirmation by the liquid chromatography was carried out in the same manner as described above.

Figure 6:
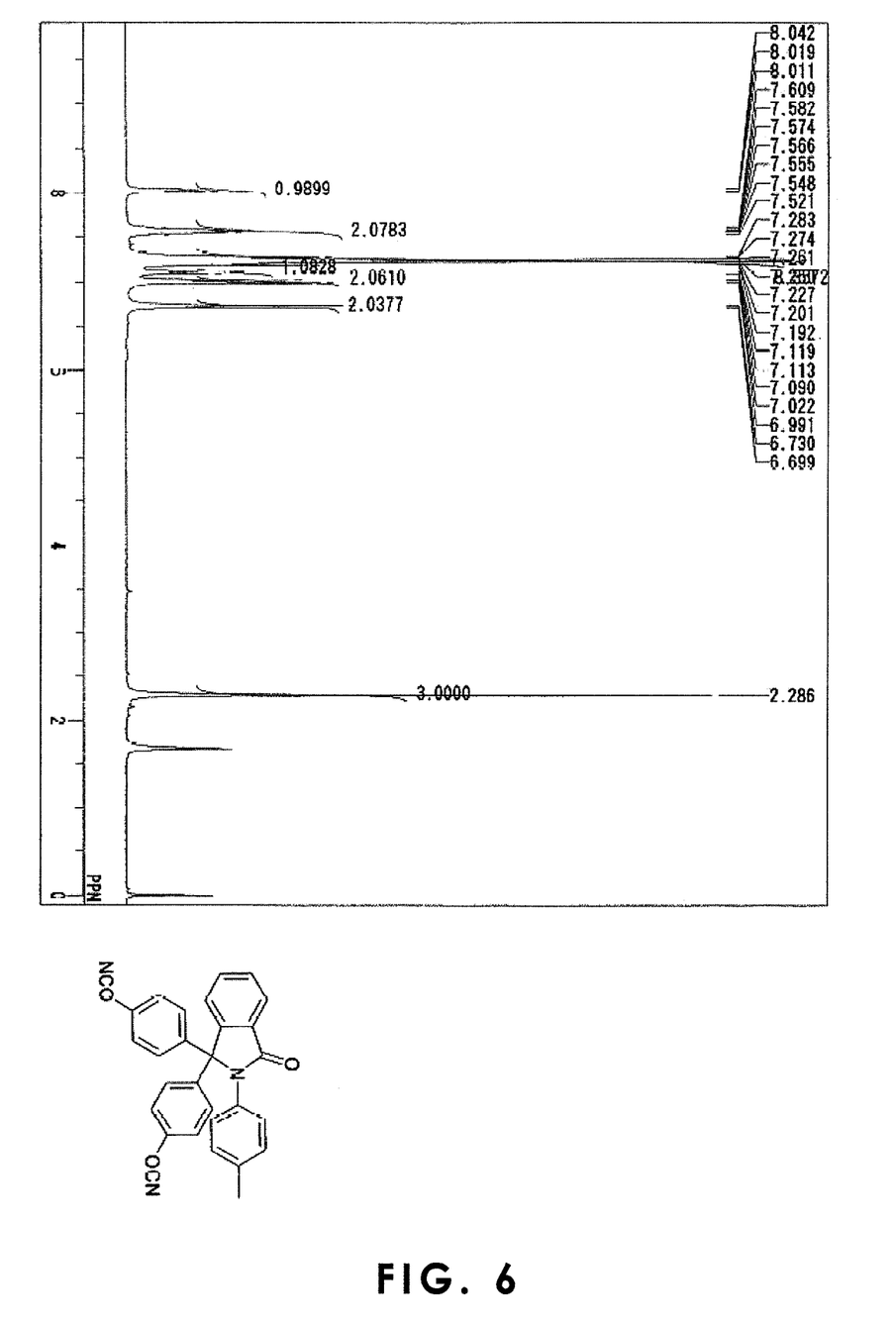
FIG. 6 is an H1-NMR chart of 2-(4-methylphenyl)-3,3-bis (4-cyanatophenyl)phthalimidine obtained in Production Example 2.

The structure of the compound thus obtained was identified by an NMR spectrum in the same manner as described above. The NMR spectrum was as shown in FIG. 6.

$^1$H-NMR: (270 MHz, chloroform-d, internal standard TMS)
δ (ppm) 2.29 (s, 3H), 6.71 (d, 2H, J=8.2 Hz), 7.01 (d, 2H, J=4.2 Hz), 7.06-7.14 (m, 1H), 7.17-7.33 (m, 8H), 7.48-7.69 (m, 2H), 7.97-8.08 (m, 1H)

Cyanate Ester Production Example 3

Synthesis of 2-phenyl-3,3-bis(4-cyanato-3-methylphenyl)phthalimidine abbreviated to BisOCR-PI-NPh-DC)

2-Phenyl-3,3-bis(4-hydroxy-3-methylphenyl)phthalimidine (30 mmol) obtained in Synthesis Example 3 was suspended in dichloromethane (90 mL). Triethylamine (90 mmol) was added to the suspension with cooling in an ice bath, and, after the completion of an exothermic reaction, the temperature of the reaction solution was raised to room temperature. Separately, 36% hydrochloric acid (90 mmol), water (50 mL), a 40% solution of cyanogen chloride (90 mmol) in dichloromethane, and dichloromethane (8 mL) were placed in a jacketed flask. Methanol of −10° C. was circulated through the jacket to cool the contents in the flask. The solution prepared above was added dropwise thereto under stirring while regulating the temperature of the contents of the flask at 0° C. or below. The reaction solution was stirred for 1 hr, and a dichloromethane (9 mL) solution of triethylamine (30 mmol) was further added dropwise thereto. The completion of the reaction was confirmed by liquid chromatography. The temperature of the reaction solution was raised to room temperature before the organic phase was separated. Cyanogen chloride was removed by distillation under the reduced pressure, and the residue was washed five times with water (100 mL). The organic phase was concentrated to obtain a product. The confirmation by the liquid chromatography was carried out in the same manner as described above.

Figure 7:
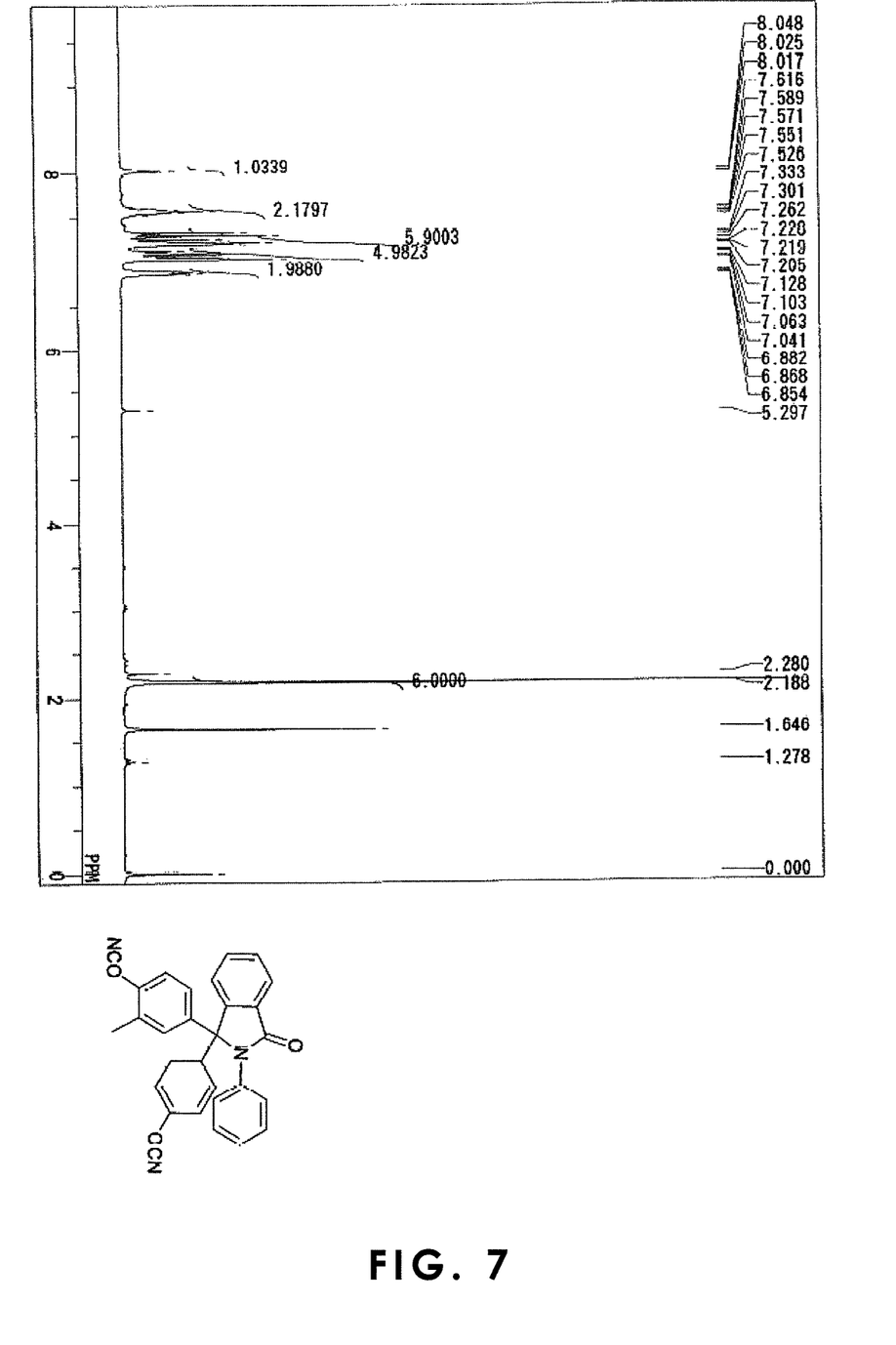
FIG. 7 is an H1-NMR chart of 2-phenyl-3,3-bis(4-cyanato-3-methylphenyl)phthalimidine obtained in Production Example 3.

The structure of the compound thus obtained was identified by an NMR spectrum in the same manner as described above. The NMR spectrum was as shown in FIG. 7.

$^1$H-NMR: (270 MHz, chloroform-d, internal standard TMS) δ (ppm) 2.19 (s, 6H), 6.82-6.93 (m, 2H), 7.00-7.15 (m, 5H), 7.17-7.35 (m, 5H), 7.50-7.63 (m, 2H), 7.99-8.07 (m, 1H)

Cyanate Ester Production Example 4

Synthesis of 1-methyl-3,3-bis(4-cyanatophenyl)indolin-2-one (abbreviated to BisP-IST-NMe-DC)

1-Methyl-3,3-bis(4-hydroxyphenyl)indolin-2-one (30 mmol) obtained in Synthesis Example 5 was suspended in DMF (50 mL). Triethylamine (90 mmol) was added to the suspension with cooling in an ice bath. Separately, a dichloromethane solution (135 mmol) of 40% cyanogen chloride and a solution of DMF (15 ml) were placed in a jacketed flask. Methanol of −10° C. was circulated through the jacket to cool the contents in the flask. The solution prepared above was added dropwise thereto under stirring while regulating the temperature of the contents of the flask at 0° C. or below. The reaction solution was stirred for 1 hr, and a DMF (10 mL) solution of triethylamine (30 mmol) was further added dropwise thereto. The completion of the reaction was confirmed by liquid chromatography. The temperature of the reaction solution was raised to room temperature. Cyanogen chloride was removed by distillation under the reduced pressure. Methylene chloride (300 ml) was added thereto, followed by washing five times with water (150 mL). The organic phase was concentrated to obtain a product. The confirmation by the liquid chromatography was carried out in the same manner as described above.

Figure 8:
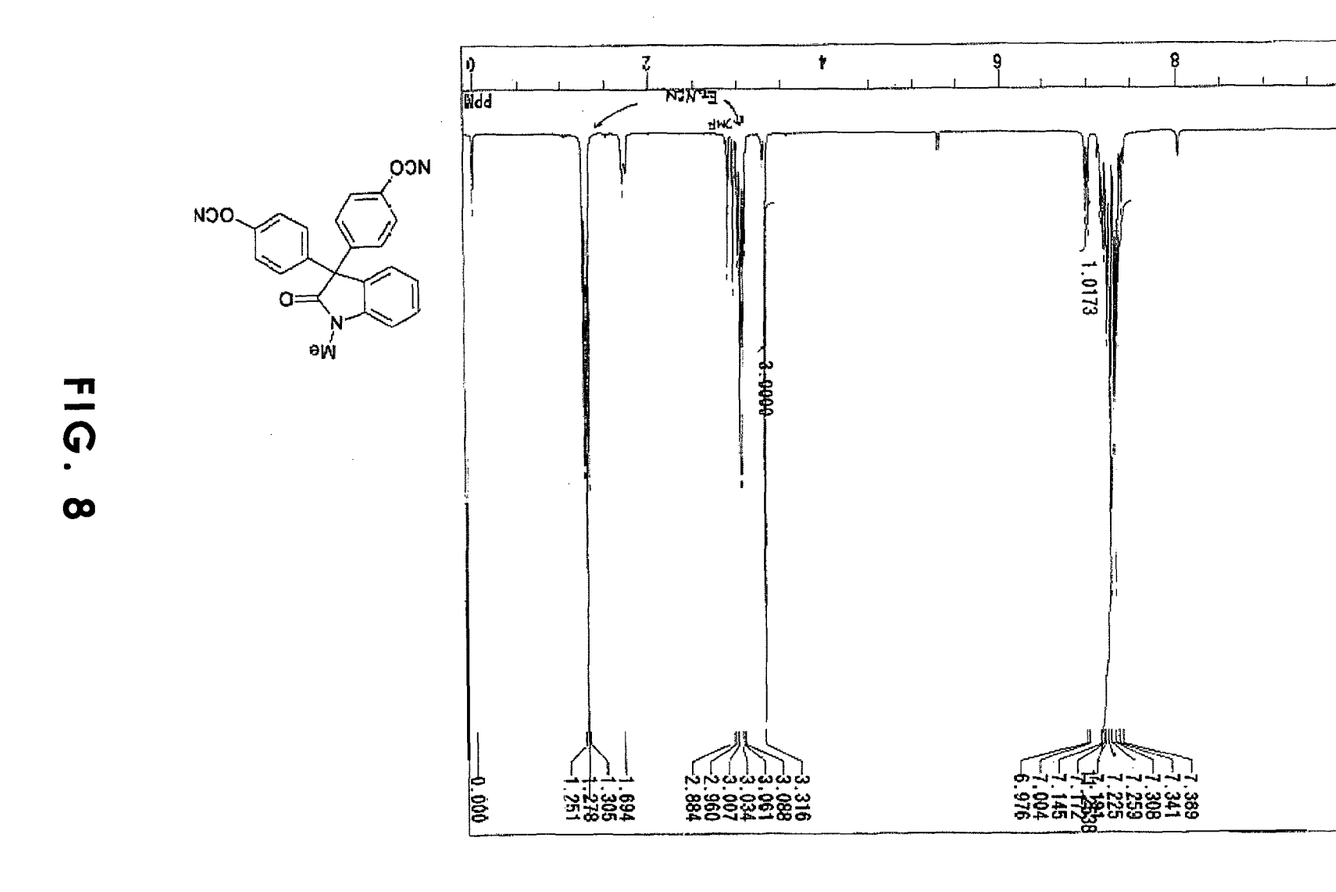
FIG. 8 is an H1-NMR chart of 1-methyl-3,3-bis(4-cyanatophenyl)indolin-2-one obtained in Production Example 4.

The structure of the compound thus obtained was identified by an NMR spectrum in the same manner as described above. The NMR spectrum was as shown in FIG. 8.

$^1$H-NMR: (270 MHz, chloroform-d, internal standard TMS)

δ (ppm) 3.32 (s, 3H), 6.99 (d, 1H, J=7.6 Hz), 7.11-7.43 (m, 11H)

Example 1

The cyanate ester (BisP-PI-NPh-DC) (30 parts by weight) obtained in Production Example 1 was mixed with 70 parts by weight of bisphenol A dicyanate (trademark: Skylex, manufactured by Mitsubishi Gas Chemical Co., Inc.; the same shall apply hereinafter). The mixture was heat-melted in an aluminum cup provided with a fluororubber O ring (S-100, manufactured by MORISEI KAKO Corporation). The interior of the aluminum cup was evacuated with a vacuum pump for degassing. The melt contained in the aluminum cup was pressed by another aluminum cup and was heated at 205° C. for 3 hr and 270° C. for 4 hr for curing. After cooling, the aluminum cup was opened to obtain a cured product of the cyanate ester compound.

Example 2

A cured product was obtained in the same manner as in Example 1, except that the cyanate ester (BisP-PI-NpTol-DC) obtained in Production Example 2 was used instead of the cyanate ester (BisP-PI-NPh-DC) used in Example 1.

Example 3

A cured product was obtained in the same manner as in Example 1, except that the cyanate ester (BisOCR-PI-NPh-DC) obtained in Production Example 3 was used instead of the cyanate ester (BisP-PI-NPh-DC) used in Example 1.

Example 4

A cured product was obtained in the same manner as in Example 1, except that the cyanate ester (BisP-IST-NMe-DC) obtained in Production Example 4 was used instead of the cyanate ester (BisP-PI-NPh-DC) used in Example 1.

Example 5

A cured product was obtained in the same manner as in Example 2, except that the amount of the cyanate ester (BisP-PI-NpTol-DC) and the amount of the bisphenol A dicyanate mixed were changed to 40 parts by weight and 60 parts by weight, respectively.

Example 6

The cyanate ester (BisP-PI-NPh-DC) (100 parts by weight) obtained in Production Example 1 was heated from room temperature at a temperature rise rate of 10° C./min and was held at 250° C. for 2 hr to obtain a cured product.

Example 7

The cyanate ester (BisP-PI-NpTol-DC) (100 parts by weight) obtained in Production Example 2 was heated from room temperature at a temperature rise rate of 10° C./min and was held at 250° C. for 2 hr to obtain a cured product.

Example 8

The cyanate ester (BisP-IST-NMe-DC) (100 parts by weight) obtained in Production Example 4 was heated from room temperature at a temperature rise rate of 10° C./min and was held at 250° C. for 2 hr to obtain a cured product.

Comparative Example 1

A cured product was obtained in the same manner as in Example 1, except that bisphenol A dicyanate (trademark: Skylex, manufactured by Mitsubishi Gas Chemical Co., Inc.) (100 parts by weight) was used instead of the mixture of 30 parts by weight of the cyanate ester with 70 parts by weight of the bisphenol A dicyanate.

<Measurement of Glass Transition Temperature>

A small piece having a size of about 50 mm×about 5 mm×about 2 mm was taken off or extracted from each of the cured products thus obtained. The small pieces were used as samples for the following glass transition temperature measurement. For the samples, the glass transition temperature was measured by the following two methods. The higher the glass transition temperature, the better the heat resistance of the cured product.

Measuring method 1: Dynamic viscoelasticity was measured with a viscoelastometer (AR2000ex, manufactured by TA INSTRUMENTS) under conditions of a strain of 0.1% and a temperature rise at a rate of 3° C./min at a frequency of 15 Hz. The maximum value of the loss tangent was regarded as the glass transition temperature.

Measuring method 2: Differential scanning calorimetry was carried out with a differential scanning calorimeter (SSC-5200, manufactured by Seiko Instruments Inc.) according to JIS (Japanese Industrial Standards) K 7121 by heating the sample at a temperature rise rate of 10° C./min to 400° C. under a nitrogen stream, then cooling the sample, and reheating the sample to 400° C. at a temperature rise rate of 10° C./min. The glass transition temperature at the middle point was regarded as the glass transition temperature.

For the cured products of Example 1 to 5 and Comparative Example 1, the glass transition temperature was measured by the measuring method 1, and, for the cured products of Examples 6 to 8, the glass transition temperature was measured by the measuring method 2. The measurement results were as shown in Table 1. In the table, numerals represent mixing amount (parts by weight).

TABLE 1

| Resin composition | | Example | | | | | | | | Comparative Example |
|---|---|---|---|---|---|---|---|---|---|---|
| | | 1 | 2 | 3 | 4 | 5 | 6 | 7 | 8 | 1 |
| Cyanate ester | BisP-Pl-NPh-DC | 30 | — | — | — | — | 100 | — | — | — |
| | BisP-Pl-NpTolNPh-DC | — | 30 | — | — | 40 | — | 100 | — | — |
| | BisOCR-Pl-NPh-DC | — | — | 30 | — | — | — | — | — | — |
| | BisP-IST-NMe-DC | — | — | — | 30 | — | — | — | 100 | — |
| | Bisphenol A dicyanate | 70 | 70 | 70 | 70 | 60 | — | — | — | 100 |
| Properties of cured product | Tg (° C.): Measuring method 1 | 302 | 318 | 297 | 309 | 339 | Not measured | Not measured | Not measured | 264 |
| | Tg (° C.): Measuring method 2 | Not measured | Not measured | Not measured | Not measured | Not measured | 381 | 349 | 341 | Not measured |

The invention claimed is:

1. A cyanate ester compound represented by general formula (1):

wherein
R1 represents an aromatic substituent having 6 to 10 carbon atoms or an alkyl group having 1 to 20 carbon atoms;
Rx1's each independently represent a hydrogen atom, an alkyl or alkoxy group having 1 to 20 carbon atoms, or a halogen;
Ry1's each independently represent a hydrogen atom, an alkyl or alkoxy group having 1 to 20 carbon atoms, or a halogen;
m is an integer of 0 to 4; and n is an integer of 0 to 4.

2. A cyanate ester compound represented by general formula (2):

wherein
R2 represents an aromatic substituent having 6 to 10 carbon atoms or an alkyl group having 1 to 20 carbon atoms;
Rx2's each independently represent a hydrogen atom, an alkyl or alkoxy group having 1 to 20 carbon atoms, or a halogen;
Ry2's each independently represent a hydrogen atom, an alkyl or alkoxy group having 1 to 20 carbon atoms, or a halogen;
m is an integer of 0 to 4; and n is an integer of 0 to 4.

3. The cyanate ester compound according to claim 1, wherein, in general formula (1), R1 represents an aromatic substituent having 6 to 10 carbon atoms or an alkyl group having 1 to 10 carbon atoms; Rx1's each independently represent a hydrogen atom, an alkyl group having 1 to 10 carbon atoms, or a halogen; and Ry1's each independently represent a hydrogen atom, an alkyl group having 1 to 10 carbon atoms, or a halogen.

4. The cyanate ester compound according to claim 1, wherein, in general formula (1), R1 represents an aromatic substituent having 6 to 10 carbon atoms or a methyl, ethyl, n-propyl, or i-propyl group; Rx1's each independently represent a hydrogen atom, an alkyl group having 1 to 5 carbon atoms, or a halogen; and Ry1's each independently represent hydrogen, an alkyl group having 1 to 5 carbon atoms, or a halogen.

5. The cyanate ester compound according to claim 1, wherein, in general formula (1), R1 represents an aromatic substituent having 6 carbon atoms or a methyl or ethyl group; Rx1's each independently represent a hydrogen atom or an alkyl group having 1 to 3 carbon atoms; and Ry1's each independently represent a hydrogen atom or an alkyl group having 1 to 3 carbon atoms.

6. The cyanate ester compound according to claim 1, wherein, in general formula (1), R1 represents a phenyl or methyl group; Rx1's each represent a hydrogen atom; and Ry1's each independently represent a hydrogen atom or a methyl group.

7. The cyanate ester compound according to claim 2, wherein, in general formula (2), R2 represents an aromatic substituent having 6 to 10 carbon atoms or an alkyl group having 1 to 10 carbon atoms; Rx2's each independently represent a hydrogen atom, an alkyl group having 1 to 10 carbon atoms, or a halogen; and Ry2's each independently represent a hydrogen atom, an alkyl group having 1 to 10 carbon atoms, or a halogen.

8. The cyanate ester compound according to claim 2, wherein, in general formula (2), R2 represents an aromatic substituent having 6 to 10 carbon atoms or a methyl, ethyl, n-propyl, or i-propyl group; Rx2's each independently represent a hydrogen atom, an alkyl group having 1 to 5 carbon atoms, or a halogen; and Ry2's each independently represent hydrogen, an alkyl group having 1 to 5 carbon atoms, or a halogen.

9. The cyanate ester compound according to claim 2, wherein, in general formula (2), R2 represents an aromatic substituent having 6 carbon atoms or a methyl or ethyl group; Rx2's each independently represent a hydrogen atom or an alkyl group having 1 to 3 carbon atoms; and Ry2's each independently represent a hydrogen atom or an alkyl group having 1 to 3 carbon atoms.

10. The cyanate ester compound according to claim 2, wherein, in general formula (2), R2 represents a phenyl or methyl group; Rx2's each represent a hydrogen atom; and Ry2's each independently represent a hydrogen atom or a methyl group.

11. A curable resin composition comprising a cyanate ester compound according to claim 1.

12. A cured product produced by curing a curable resin composition according to claim 11.

\* \* \* \* \*